(12) United States Patent
Rozas Andreu et al.

(10) Patent No.: US 10,508,297 B2
(45) Date of Patent: Dec. 17, 2019

(54) METHOD FOR IMMOBILIZATION OF GLUCURONIDASE ENZYMES FOR THE DETECTION OF PRODUCTS DERIVED FROM GLUCURONIDE COMPOUNDS

(71) Applicant: LA PIEDRA BIOTECNOLOGÍA SPA, Puerto Varas (CL)

(72) Inventors: Manuel Rozas Andreu, Puerto Varas (CL); Fernando Alexis Gutierrez Rojas, Puerto Varas (CL); Rocio Andrea Peralta Villalobos, Puerto Varas (CL)

(73) Assignee: LA PIEDRA BIOTECNOLOGÍA SPA, Puerto Varas (CL)

( * ) Notice: Subject to any disclaimer, the term of this patent is extended or adjusted under 35 U.S.C. 154(b) by 0 days.

(21) Appl. No.: 15/649,538

(22) Filed: Jul. 13, 2017

(65) Prior Publication Data
US 2019/0017094 A1 Jan. 17, 2019

(51) Int. Cl.
*C12Q 1/40* (2006.01)

(52) U.S. Cl.
CPC ........ *C12Q 1/40* (2013.01); *C12Y 302/01031* (2013.01); *G01N 2333/924* (2013.01); *G01N 2400/00* (2013.01)

(58) Field of Classification Search
CPC .............. C12Q 1/40; C12Y 302/01031; G01N 2333/924; G01N 2400/00
USPC ...................................................... 435/174
See application file for complete search history.

(56) References Cited

U.S. PATENT DOCUMENTS

| 5,739,004 A | 4/1998 | Woodson |
| 2016/0076075 A1 | 3/2016 | McIntire et al. |

FOREIGN PATENT DOCUMENTS

| WO | 2003076640 | 9/2003 |
| WO | 2013123253 | 8/2013 |

OTHER PUBLICATIONS

Brady et al., Advances in enzyme immobilization, Biotechnol Lett, (2009) 31:1639-1650.*
Vieira et al., β-Glucosidase immobilized and stabilized on agarose matrix functionalized with distinct reactive groups, Journal of Molecular Catalysis B: Enzymatic, 69 (2011), pp. 47-53.*
Sigma-Aldrich, Product No. 408727, Polyethylenimine, branched, Accessed Feb. 3, 2018, Available Online at: www.signnaaldrich.com/catalog/product/aldrich/408727?lang=en&region=US.*
ABT, Your agarose beads for separation, purification and conjugation of biomolecules, 2015, Available online at: www.chemie-brunschwig.ch/docunnents/suppliers-information/ABT-Brochure-2015-1.pdf.*
Kura Biotec, Beta-glucuronidases, The New Generation BGTurbo, Available at least as early as Aug. 16, 2016, per Internet Archive, Available online at: web.archive.org/web/20160816053619/http://www. kurabiotec.com:80/products/bgluc-newgeneration/.*
Rowland, Andrew, et al., "The UDP-glycuronosyltransferases: Their role in drug metabolism and detoxification", 12 pages. Mar. 7, 2013. The International Journal of Biochemistry & Cell Biology 45 (2013) 1121-1132. Copyright 2013 Elsevier Ltd. 1357-2725.
Fox, E.J., et al., "Quantitative Analysis of Buprenorphine and Norbuprenorphine in Urine using Liquid Chromatography Tandem Mass Spectrometry", 7 pages. Journal of Analytical Toxicology, vol. 30, May 2006.
Arroyo, Dr. Miguel, "Immobilized Enzymes: Theory, Methods of Study and Applications". 17 pages. Untranslated. Ars Pharmaceutica, 39:2; 23-39, 1998.
Guisan, Jose M., Editor, "Immobilization of Enzymes and Cells", Second Edition, 146 pages. Methods in Biotechnology TM 22, Copyright 2006, Humana Press, Inc., Totowa, NJ ISBN 1-58829-290-8.
Mateo, Cesar, et al., "Improvement of enzyme activity, stability and selectivity via immobilization techniques", 14 pages. Enzyme and Microbial Technology 40, May 2007. Elsevier.
Brady, Dean, et al., "Advances in Enzyme Immobilisation", 36 pages. Biotechnology Letters 2009. Section: Microbial and Enzyme Technology Review. CSIR Biosciences, South Africa. Department of Biotechnology and Food Technology, Tshwane University of Technology, Pretoria, South Africa.
Rocha-Martin, Javier, et al., "New Biotechnological perspectives of a NADH oxidase variant from Thermus thermophilus HB27 as NAD+—recycling enzyme". 11 pages. BMC Biotechnology 2011, 11:101 http://www.biomedcentral.com/1472-6750/11/101. Copyright 2011 Rocha-Martin et al. Licensee: BioMed Central Ltd.
Singh, Raushan Kumar, et al., "From Protein Engineering to Immobilization: Promising Strategies for the Upgrade of Industrial Enzymes". 46 pages. International Journal of Molecular Sciences ISSN 1422-0067. Int. J. Mol. Sci. 2013, 14, 1232-1277; doi: 10.3390/ijms14011232.
Rapatz, E., et al., "Studies on the Immobilization of Glucuronidase (Part 2)—Cleavage of Hardly Soluble Substrates in Organic Solvents". 8 pages. Copyright 1988 The Humana Press Inc. Totowa, NJ. 0273-2289/88/1903-0235. Applied Biochemistry and Biotechnology, vol. 19, 1988.
Zdarta, J., et al., A General Overview of Support Materials for Enzyme Immobilization: Characteristics, Properties, Practical Utility, Catalysts, Feb. 24, 2018, 8(92), 27 pgs.

* cited by examiner

*Primary Examiner* — Jennifer M. H. Tichy
(74) *Attorney, Agent, or Firm* — Procopio, Cory, Hargreaves & Savitch LLP

(57) ABSTRACT

The present invention provides an insoluble enzymatic reagent for detecting products derived from glucuronide metabolites in a sample, containing an enzyme with glucuronidase activity immobilized on a resin comprising a polysaccharide modified with chemical groups, and optionally a cationic polymer. Additionally, it provides methods for preparing said enzymatic reagent and for detecting derivatives of glucuronide metabolites in a sample, using said reagent.

16 Claims, 10 Drawing Sheets

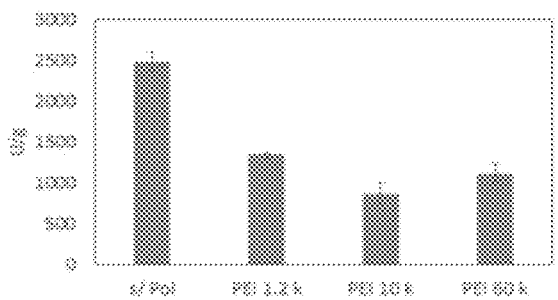
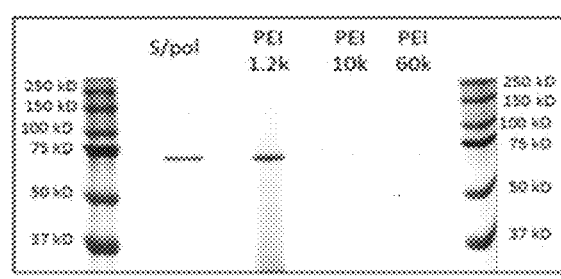
FIG. 5A  FIG. 5C
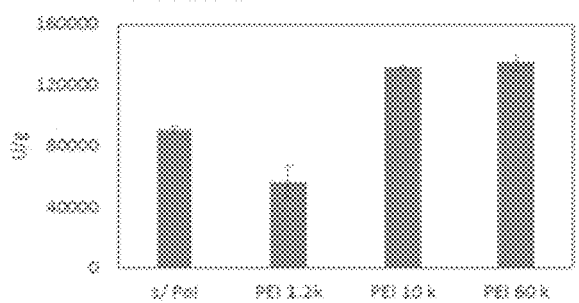
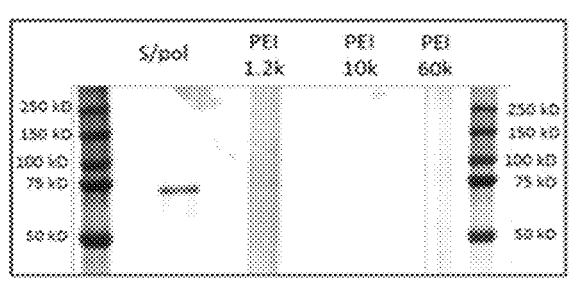
FIG. 5B  FIG. 5D

Parameters for
inactivation model

| BGTurbo | $k_1$ (h$^{-1}$) | $R^2$ | $t_{½}$ (h) |
|---|---|---|---|
| Soluble | 0.653 | 0.95 | 1.06 |
| Immobilized | 0.130 | 0.96 | 5.33 |

_US 10,508,297 B2_

METHOD FOR IMMOBILIZATION OF GLUCURONIDASE ENZYMES FOR THE DETECTION OF PRODUCTS DERIVED FROM GLUCURONIDE COMPOUNDS

TECHNICAL FIELD

The present invention relates to the technical field of biotechnology, and in particular provides a method for the immobilization and stabilization of enzymes, and especially of glucuronidase enzymes for the detection of products derived from glucuronide compounds present in a sample, using for this purpose a β-glucuronidase enzyme; as well as a reagent including said immobilized and stabilized enzyme.

BACKGROUND OF THE INVENTION

Toxicological research uses different analytical techniques for the quantification of compounds of interest which are detrimental to the organism. These techniques become even more relevant when detecting the use of illicit substances is needed, or detecting drugs, toxins or pollutants in biological samples.

Glucuronidation of chemical compounds is an essential part of the metabolism of toxic substances to facilitate their excretion of the organism. During this process, biochemical reactions occur which eventually give rise to glucuronide compounds, i.e., metabolites to which glucuronic acid has been conjugated by means of a covalent bond. This biological process has been extensively documented, as shown in Rowland, A. et al. (2013), _The UDP-glucuronosyltransferases: their role in drug metabolism and detoxification_, The International Journal of Biochemistry & Cell Biology, 45 (6), 1121-1132.

For the identification and quantification of glucuronide metabolites in biological fluids, enzymatic hydrolysis methods are used which consist of the use of glucuronidases from different origins. As an example, US patent application 20160076075 A1 discloses a method of enzymatic hydrolysis of glucuronide metabolites.

As a product of the reaction catalyzed by these enzymes, the glucuronide metabolites are degraded to their corresponding aglycones and glucuronic acid, which are subsequently detected by analytical techniques, as shown in Fox, E. et al. (2006), _Quantitative analysis of buprenorphine and norbuprenorphine in urine using liquid chromatography tandem mass spectrometry_, Journal of Analytical Toxicology, 30 (4), 238-244. The glucuronidase enzymes used for these purposes can be obtained from various organisms, such as _Escherichia coli_, _Patella vulgata_, _Helix pomatia_, _Haliotis rufescens_ and from bovine liver (Kemp, P M and Cliburn, K D (2015), _Comparison of Species-Specific β-Glucuronidase Hydrolysis of Cannabinoid Metabolites in Human Urine_ (No. DOT/FAA/PM-15/6)). Recently, a β-glucuronidase derived from _Brachyspira pilosicoli_ bacterium has been reported (patent application GB1614546.8 (2016), Kura Biotec).

Once the biological sample containing the glucuronide metabolites is enzymatically hydrolyzed, there are different analytical techniques for the detection of the products of said hydrolysis, in which liquid chromatography coupled to mass spectrometry (LC-MS/MS as the initials of Liquid Chromatography-Mass Spectrometry) is one of the most commonly used. However, these applications generally use stages of sample preparation based on liquid-liquid extraction (LLE, as the initials of Liquid-Liquid Extraction; or SLE, for Supported Liquid Extraction) or solid phase extraction (SPE as the initials of Solid Phase Extraction, DPX (Disposable Pipette tip Extraction), as described in PCT patent application WO2013123253) as pre-chromatographic analysis, to clean impurities from the sample in order to prevent contaminants produced by metabolism that may interfere or affect the subsequent analysis. Although improvements have been made to facilitate the detection process of the compounds of interest, by eliminating the pre-analysis extraction step, such as the dilution and injection method (DS, dilute and Shoot LC-MS) (Deventer, K. et al. (2014), _Dilute-and-shoot-liquid chromatography-mass spectrometry for urine analysis in doping control and analytical toxicology_, Trac Trends in Analytical Chemistry, 55, 1-13) or removing the enzyme added in the hydrolysis step (β-Gone™, Phenomenex), these techniques generate loss of sensitivity in quantitation due to high dilution and retard the process of analysis, since an additional step must be considered.

The implementation of enzymes on an industrial scale previously requires the improvement of the catalytic properties of the same, since the majority of the enzymes are not stable in the working conditions. When enzymes are soluble in aqueous solutions, their separation from the substrates and products is difficult, which therefore limits their reutilization. In particular, for the purpose of drug analysis in biological samples, the enzymes used in the hydrolysis of the glucuronide metabolites, when found free in solution, obstruct the analysis columns and decrease the concentration of the enzyme available for the reaction, interfering in the final step of quantification. Moreover, multimeric enzymes can be dissociated in their subunits, depending on the dilution and pH when soluble, as it is the case of β-glucuronidase enzymes.

Due to the above, the soluble enzymes must be immobilized to allow their use for prolonged periods. In this way, the immobilization of enzymes is a process in which they are fixed in a support to give rise to insoluble forms able to maintain their catalytic activity and to increase their stability (Arroyo, M. (1998), _Inmovilización de enzimas. Fundamentos, métodos y aplicaciones_, Ars Pharvaceutica, 39 (2), 23-39). Although immobilization of enzymes is generally considered to improve their stability in general, this does not always occur if the immobilization has not been properly designed, and it may even be decreased if the support produces undesired interactions with the enzyme (Mateo, C. et al. (2007), _Improvement of enzyme activity, stability and selectivity via immobilization techniques_, Enzyme and microbial Technology, 40 (6), 1451-1463).

Regarding the immobilization of enzymes, the book of Guisan, J. M. (2006. _Immobilization of enzymes and cells_. Second Edition. Methods in Biotechnology; 22. Humana Press. 465 p. Chapter 1: _Immobilization of enzymes as the 21st Century begins: an already solved problem or still an exciting challenge?_) suggests that many companies can produce enzymes, however they are not capable of producing them in supports because the development of protocols for the immobilization of enzymes is critical. It also indicates that enzymes possess amino acid residues that are capable of interacting, either by adsorption or covalently, with the immobilization supports by means of different mechanisms and, therefore, protocols are required that are efficient for each enzyme in terms of its activity, stability, selectivity and absence of inhibitors.

The state of the art is broad in relation to enzyme immobilization techniques in general. The publication Brady, D. and Jordaan, J. (2009. _Advances in enzyme immobilisation. Biotechnology Letters_, 31 (11), 1639) describes supports for immobilization of enzymes, wherein commercial resins are disclosed and microcapsules, dendrispheres or spherenzymes, among others.

As is well known in the field of biochemistry, the structure of an enzyme, whether its composition of amino acid residues and the three-dimensional conformation of these differ from one to another. The publication of Singh, R. K. et al (2013), *From engineering to protein immobilization. Promising strategies for the upgrade of Industrial enzymes, International Journal of Molecular Sciences,* 14 (1), 1232-1277, describes that the content of lysine residues affects the binding of an enzyme to glutaraldehyde-agarose resins and that, therefore, variations in lysine content may produce differences in enzyme immobilization since conformational changes can occur, altering the affinity for the substrate.

PCT application WO 03/076640 describes the immobilization of the enzyme D-amino acid oxidase (DAAO) originated from *Rhodotorula dracilis* or *Trigonopsis variabilis* on agarose modified with glyoxyl groups, wherein it was observed that the *R. dracilis* enzyme was considerably more stabilized than the enzyme originated from *T. variabilis*, indicating that the same immobilization protocol does not necessarily work for the same enzyme of any origin.

The publication of Rocha-Martin, J. et al. (2011), *New perspectives of biotechnological NADH oxidase from Thermus thermophilus H827 variant as NAD +-recycling enzyme, BMC Biotechnology* 11 (1), 101 describes the immobilization of the enzyme NADH oxidase (NOX) on agarose activated with glyoxyl groups, in which the binding was performed through its regions rich in lysine residues, resulting in strong covalent bonds. This work shows that, depending on the protocol used, the immobilization and the enzymatic activity achieved vary.

Regarding the immobilization of glucuronidase enzymes, the document published by Rapatz, E. et al. (1988), *Studies on the immobilization of glucuronidase (Part 2), Applied Biochemistry and Biotechnology,* 19 (3), 235-242 indicates that β-glucuronidase is a multimeric enzyme that can dissociate into its subunits, depending on dilution and the pH when being soluble. To prevent dissociation of the enzyme, immobilization of β-glucuronidase from *Helix pomatia* in bovine serum albumin and crosslinking with glutaraldehyde was tested, which achieved stabilization of the enzyme. Subsequently, U.S. Pat. No. 5,739,004 generally discloses supports for immobilization of enzymes, including β-glucuronidase derived from microorganisms capable of forming spores, such as *Candida, Bacillus, Neurospora* and *Clostridium*; where agarose, cellulose and dextran are mentioned, among others.

The state of the art indicates that, depending on the desired application, it is necessary to define a specific immobilization protocol to increase the stability of an enzyme, in which it is necessary to control parameters such as temperature, pH, size and particular characteristics of the polymers used, etc. In particular for analysis of glucuronide metabolites present in biological samples, considering the above background there is a significant need to provide supports for the immobilization of enzymes that increase their stability to facilitate the degradation of these compounds, in order to accelerate the processes of analysis and quantification of drugs and toxins, among others.

SUMMARY OF THE INVENTION

The present invention provides an insoluble enzymatic reagent for the detection of products derived from glucuronide metabolites in a sample, comprising an enzyme with glucuronidase activity immobilized on a resin of a polysaccharide activated with a chemical functional group which is selected from the group consisting of: aldehyde, amino and hydroxysuccinimide or a combination thereof. Optionally, the resin includes the enzyme cross-linked with polyethyleneimine. In a preferred embodiment, the enzyme with glucuronidase activity is a β-glucuronidase originated from a bacterium of the genus *Brachyspira* sp.

Preferably, the insoluble enzymatic reagent contains the immobilized enzyme in the range from 0.1 to 10 mg per gram of resin; the polysaccharide is agarose having a particle size between 40 and 250 µm; and the aldehyde groups are glyoxyl groups in a concentration from 10 to 100 µmol/mL of agarose gel. Still more desirably, the polyethyleneimine is a branched polymer and has a number average molecular weight from 1 to 100 kDa; and a weight average molecular weight from 1 to 1,000 kDa. Additionally, the weight/weight (w/w) ratio between the polysaccharide and the polyethyleneimine is from 20:1 to 4:1.

A second object of the present invention is a method for preparing an insoluble enzymatic reagent for the detection of products derived from glucuronide metabolites in a sample comprising the steps of: (i) providing an enzyme with glucuronidase activity; (ii) providing a resin of a polysaccharide activated with a functional chemical group which is selected from the group consisting of: aldehyde, amino and hydroxysuccinimide or a combination thereof; and (iii) immobilizing the enzyme from step (i) by mixing it with the resin of step (ii). Optionally, the method includes the following steps after immobilization of the enzyme: (iv) adding to the mixture of step (iii) a solution of polyethyleneimine as a stabilizing agent, and (v) adding a reducing chemical agent.

Preferably, the enzyme with glucuronidase activity is a β-glucuronidase derived from a bacterium of the genus *Brachyspira* sp and it is provided in a solution from 0.01 to 10 mg/mL at alkaline pH from 7 to 11. In a desired embodiment, the polysaccharide is agarose with a particle size between 40 and 250 µm; which is preferably activated with aldehyde groups, specifically glyoxyl groups; and the weight/weight (w/w) ratio of the mixture between the aldehyde-activated polysaccharide and the enzyme is from 10,000:1 to 20:1. Additionally, the polyethyleneimine solution has a concentration from 1 to 100 mg/mL at alkaline pH between 7 and 11; and the preferred reducing chemical agent is a metal borohydride.

A third object of the invention encompasses a method for the detection of products derived from glucuronide metabolites in a sample with an insoluble enzymatic reagent, comprising the steps of: (i) providing the sample in which said derivative is to be detected; (ii) contacting said sample with an insoluble enzymatic reagent comprising an enzyme having glucuronidase activity immobilized on a resin of a polysaccharide activated with a chemical functional group selected from the group consisting of: aldehyde, amino and hydroxysuccinimide or a combination thereof; (iii) incubating the sample with said reagent for a determined period; and (iv) detecting the derivative of said glucuronide metabolite by a suitable technique. In a preferred embodiment, between the steps of incubating the sample and detecting the derivative of said glucuronide metabolite it is included a step of cleaning the sample through an extraction column which is selected from the group consisting of: solid phase extraction, liquid-liquid and solid-liquid extractions. The suitable technique is selected from the group consisting of: chromatography, spectrometry, immunoassays or a combination thereof.

BRIEF DESCRIPTION OF THE FIGURES

FIGS. 5A and 5B show the enzymatic activity of the BG100® and BGTurbo™ enzymes, respectively, stabilized with polyethyleneimine of different sizes. FIGS. 5C and 5D show SDS-PAGE gels to evaluate enzymatic stability.

DETAILED DESCRIPTION OF THE INVENTION

Figure 1:
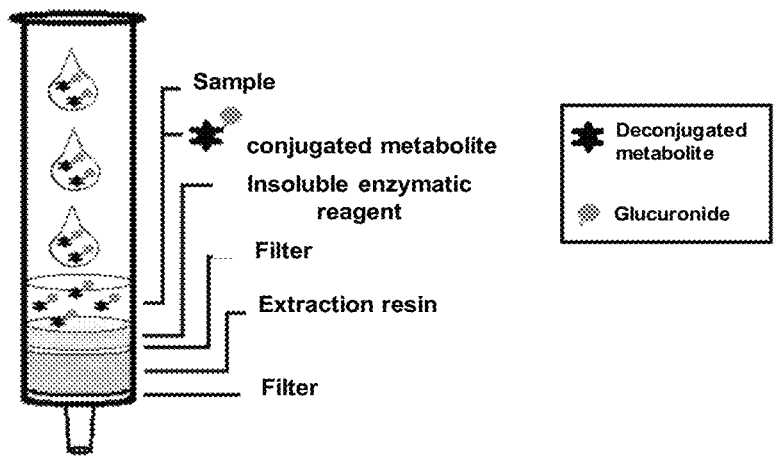
FIG. 1 shows a solid phase extraction column (SPE/SLE) to which a glucuronidase enzyme immobilized on a resin has been incorporated as an insoluble enzymatic reagent for the hydrolysis of compounds conjugated with glucuronides.
Figure 1:
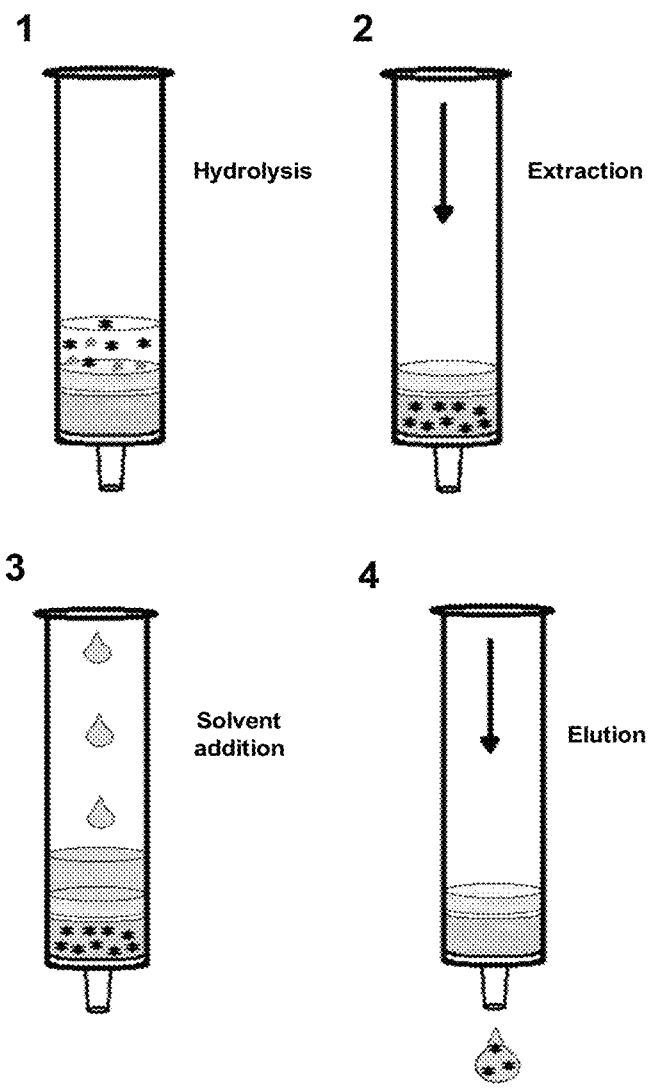

The present invention provides an insoluble enzymatic reagent for the detection of products derived from glucuronide metabolites in a sample comprising an enzyme with β-glucuronidase activity immobilized on a resin of a polysaccharide activated with a chemical functional group which is selected from the group consisting of: aldehyde, amino and hydroxysuccinimide or a combination thereof. In a preferred embodiment, the resin also includes the polyethyleneimine polymer to stabilize the immobilized enzyme. Further, the invention provides a method for preparing the insoluble enzyme reagent for the detection of said glucuronide metabolite derivatives in a sample; and a method for the detection of products derived from glucuronide metabolites in a sample using said insoluble enzymatic reagent.

The insoluble enzymatic reagent together with the method for its preparation and the method for the detection of products derived from glucuronide compounds of the present invention allow to considerably simplify the hydrolysis process, to avoid contamination of the sample with the soluble enzyme, to reduce the complexity of the analysis process of derivatives of glucuronide compounds since the number of stages of the process is reduced to only one: passing a sample through a substrate in a column, facilitating its manipulation. In addition, immobilization of enzymes with glucuronidase activity allows to extend the range of buffer solutions to be used, since it makes enzymes more stable against changes in pH and temperature. These factors make the proposed insoluble enzymatic reagent more compatible with quantitation systems, such as those of dilution and injection (Dilute & Shoot) and chromatographic analysis and mass spectrometry.

All technical and scientific terms used to describe the present invention have the same meaning as understood for a person having basic knowledge in the technical field in question. In order to define the invention more clearly, the following terms will be understood as defined below.

The term "glucuronide metabolite" refers to any compound conjugated with glucuronic acid via a glycosidic bond. It should be understood that a glucuronide metabolite may be natural or synthetic, produced by chemical or enzymatic methods.

The terms "conjugate compound", "conjugated metabolite", "glucuronide compound", "glucuronide substrate" are used interchangeably to describe part of the technical features of the present invention.

It should be understood by "derivative of glucuronide metabolites", "product derived from glucuronide metabolites" or "deconjugated metabolite" as the molecule obtained as the product of the hydrolysis or breakdown of the glycosidic bond or linkage of a glucuronide metabolite, generally known as aglycone.

The term "insoluble enzymatic reagent" or "insoluble enzyme reagent" refers to an enzyme immobilized on any support, such that it is not soluble or free in solution.

The term "support", and the equivalents "resin" or "matrix", are understood as that material enabling the immobilization of a component of interest in or on it, preferably an enzyme within the scope of the present invention.

The term "extraction column" is understood as an adsorbent material which retains on its surface different components of a sample, allowing its separation therefrom. Usually said material is contained in a tube, cartridge, pipette tips, among others.

The term "hydrolysis column", in the context of the present invention, is understood as a tube or cartridge containing an insoluble enzymatic reagent which allows the hydrolysis or rupture of the glycosidic bond of a glucuronide compound.

The term "biological sample" is defined as that material derived from tissues or fluids of a living being obtained for analysis, such as, for example: saliva, blood, plasma, urine, hair, skin, tooth, soft tissues, semen, sweat, cerebrospinal fluid, fecal matter, meconium or vitreous humor, among others. In the context of the present invention, the biological sample may optionally be diluted in a buffer solution prior to analysis.

The term "crosslinking" of a polymer molecule is understood as the bond between a portion or chain of said polymer with another chain or portion of the same molecule or another.

The first object of the invention is an insoluble enzymatic reagent, comprising an enzyme having glucuronidase activity immobilized on a resin of a polysaccharide activated with a functional chemical group selected from the group consisting of: aldehyde, amino and hydroxysuccinimide, or a combination thereof; and optionally cross-linked with polyethyleneimine, which allows the stabilization of the enzyme. The resin employed in the present invention enables immobilization of enzymes with glucuronidase activity, and preferably β-glucuronidase activity. Said enzymes may be obtained from different sources, such as from bacteria, molluscs, bovine liver or other origins. In the commerce, these enzymes are marketed as: BGTurbo™ (*Brachyspira pilosicoli*, KuraBiotec), β-glucuronidase from *Escherichia coli*, Patella vulgate and from bovine liver (Sigma Aldrich); and *Haliotis rufescens* (BG100®, KuraBiotec; BETA-GLUC100™, Ango). In a preferred embodiment, the immobilized enzyme is originated from *Brachyspira pilosicoli* (patent application GB1614546.8 (2016), KuraBiotec) since it has demonstrated a superior hydrolysis capacity when compared to other commercially available enzymes. The concentration of the immobilized enzyme is in the range from 0.1 to 10 mg per gram of resin.

The insoluble enzymatic reagent and the method for immobilizing the enzymes with glucuronidase activity of the present invention allow to fix enzymes having a low lysine content, whose immobilization was very complex before, on a physical support. For example, the lysine content of the β-glucuronidase from red abalone (*Haliotis rufescens*) is 40 residues in 625 aminoacids (aa), equivalent to 6.4%, whereas *E. coli* is 40 residues in 603 aa, equal to 6.6%. In the case of *Brachyspira pilosicoli*, the lysine content of β-glucuronidase is 29 in 603 aa residues, equivalent to 4.8%.

The polysaccharide polymer of the resin of the present invention is selected from the group consisting of: agarose, dextran, alginate, cellulose, starch or another that can be chemically modified to generate aldehyde groups. The polysaccharides may be employed in any form, such as gel, particles, microcapsules, or may be activated or crosslinked with each other or with other molecules. Optionally, they can be chemically treated to add functional groups that optimize the enzymatic immobilization process. Preferably, the polysaccharide is agarose (Sepharose™) with a particle size between 40-250 μm, preferably between 45 and 165 μm.

The polysaccharide of the resin of the present invention is chemically modified to obtain aldehyde groups on the surface thereof. Said aldehyde groups are preferably glyoxyl groups. In a preferred embodiment, said glyoxyl groups are in a concentration between 10 and 100 μmol/mL of gel. In other preferred embodiments, polysaccharides modified with chemical functional groups such as amino ($NH_2$) and N-hydroxysuccinimide (NHS) can be used.

In an even more preferred embodiment, the enzyme is originated from *Brachyspira pilosicoli* and it is immobilized on a resin of a polysaccharide, preferably agarose, activated with aldehyde groups, preferably glyoxyl groups; and it is crosslinked with polyethyleneimine.

In a preferred embodiment, the polyethyleneimine forming part of the resin of the present invention is a polymer which may be used in a linear, branched or dendrimeric form. Preferably, branch-shaped polymers are used, having a number average molecular weight between 1 and 100 kDa, even more preferably 60 kDa, by gel filtration chromatography; and a weight average molecular weight from 1 to 1,000 kDa, more preferably 750 kDa, by static light scattering. Polyethyleneimine can be replaced by another polymer, preferably polycationic, which allows the stabilization of the enzyme. The resin allowing the immobilization of an enzyme with glucuronidase activity of the present invention has a weight-to-weight ratio between the polysaccharide and polyethyleneimine between 20:1 and 4:1, preferably 8:1.

The insoluble enzymatic reagent of the present invention, which comprises an immobilized glucuronidase enzyme for the hydrolysis of glucuronide metabolites, can be used alone to hydrolyze biological samples or can be implemented as part of various types of extraction columns for subsequent quantification and analysis of the compounds of interest, whether in manual or automated systems. In a first preferred embodiment, said insoluble enzyme reagent is implemented as a resin in an SPE column (Solid Phase Extraction), SLE (Supported Liquid Extraction) LLE (Liquid-Liquid Extraction) or DPX (Disposable Pipette Tip Extraction), or variants thereof.

The insoluble enzymatic reagent of the invention may be positioned on, above or under the extraction resin of the SPE and SLE columns, preferably on these columns. The biological sample to be analyzed is charged into the column and flows through both resins, occurring in the first place the hydrolysis reaction and the release of the deconjugated metabolite; and secondly the extraction in SPE or SLE resins, as shown in FIG. 1. When using columns DPX (Disposable Pipette Tip Extraction), the insoluble enzyme reagent is mixed with the extraction resin, producing together the hydrolysis and extraction processes in a single stage of homogenization, according to FIG. 2. Regardless of the type of column used, finally the metabolite that has been hydrolyzed and fixed in the extraction resin is eluted from the column for further analysis by chromatography coupled to mass spectrometry, or any other technique that allows its detection and quantification. Examples of extraction columns which can use the insoluble enzymatic reagent of the present invention are: SPE cartridges, SPE dispersive, Sigma-Aldrich™; ITSP™-SPE (itspsolutions.com); SLE ISOLUTE™ columns (biotage.com); DPX™ extraction pipette tips (dpxtechnologies.com); DPX, GERSTEL™; among others.

Figure 3A:
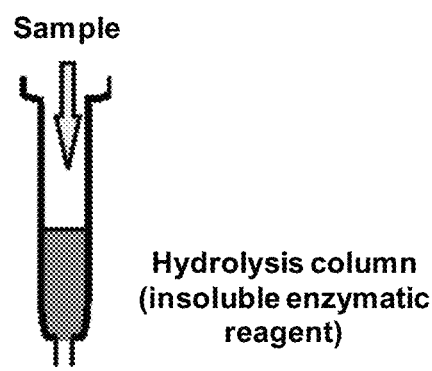
FIG. 3A shows an application of the insoluble enzymatic reagent as a hydrolysis column.

In a second preferred embodiment, the insoluble enzymatic reagent of the present invention is implemented in a column exclusively for hydrolysis. This modality works by using the enzymatic reagent as the solid phase of the column. The biological sample is loaded onto the column as shown in FIG. 3A and hydrolyzed by the catalytic action of the immobilized enzyme. The hydrolyzed metabolites leave the column as a reaction product, which can be subjected to purification or extraction steps; or may be processed by a method of dilution and injection (Dilute & Shoot), thus eliminating the need to dilute the sample product of the addition of the enzyme, if it had been used in soluble form.

Figure 3B:
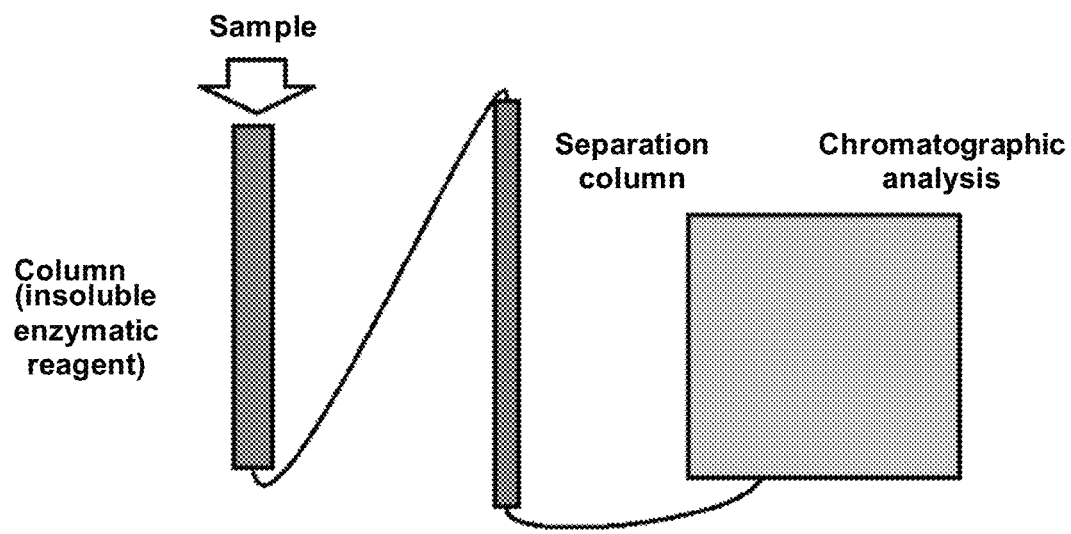
FIG. 3B shows an application of the insoluble enzymatic reagent as part of a system coupled in line to an extraction column and to a means for quantifying the samples.

In a third preferred embodiment, the proposed insoluble enzymatic reagent may be implemented in a reusable column, or in a series or parallel column system. Each hydrolysis column can be washed after each cycle with solvents able to remove all contaminants, such as water, acetic acid, ammonium acetate, methanol, hexane, among others. Optionally, the column container can be discarded after use as a disposable column. Subsequently, the hydrolyzed sample can be analyzed by the dilution and injection technique (Dilute & Shoot), or subjected to an extraction step and subsequent chromatographic analysis, as indicated in FIG. 3B in a continuous system, with other analytical techniques.

A second object of the invention relates to a method for preparing the insoluble enzymatic reagent for the detection and analysis of derivatives of glucuronide metabolites in a biological sample. First, an enzyme with glucuronidase activity is provided, preferably of the genus *Brachyspira*, and more preferably of the species *Brachyspira pilosicoli*, in solution between 0.01 and 10 mg/mL at alkaline pH, between 7 and 11. An aldehyde group-activated polysaccharide resin is provided, preferably glyoxyl-group-modified agarose in a concentration from 10 to 100 μmol/mL of gel and is mixed with the enzyme to immobilize it in a weight/ weight proportion of mixture between the polysaccharide activated with aldehyde groups and the enzyme between 10,000:1 to 20:1, preferably 500:1. In a preferred embodiment, optionally, and subsequent to the above steps, a solution of polyethyleneimine as stabilizing agent is added to the above mixture; and finally, a reducing agent is added in order to reduce and stabilize the amine bonds formed, wherein further the remaining aldehyde groups are converted into inert hydroxyl groups. Said reducing agent is preferably a metal borohydride, most preferably sodium borohydride ($NaBH_4$). In another preferred embodiment, the polymer of polyethyleneimine is added during the process of immobilization of the enzyme to the support or resin.

A third object of invention of the present application is a method for detecting derivatives of glucuronide metabolites in a sample, which requires contacting the sample with the insoluble and immobilized enzymatic reagent of the present invention. The sample and the reagent containing the enzyme are incubated for a certain time, between 1 and 30 minutes. When the resin is used as a hydrolysis column, the incubation time can be reduced to between 0.5 to 10 minutes, depending on the glucuronidase activity of the enzyme used. In a preferred embodiment, the enzyme used is the β-glucuronidase from *Brachyspira pilosicoli* (BG-Turbo™, KuraBiotec), which can reduce the incubation time for hydrolysis to 2.5 minutes. Later, the hydrolyzed sample is subjected to analysis, either for detection or quantification of the deconjugated compound, by chromatographic, spectrophotometric or immunological techniques. Preferably, such techniques are liquid chromatography and mass spectrometry analysis. Optionally, before subjecting the hydrolyzed sample to analysis and quantification, it can be concentrated and cleaned of undesirable compounds to be passed through an extraction column, which is selected from the group consisting of solid phase extraction, liquid-liquid or solid-liquid extraction, or any other that enables retention or washing of unwanted compounds to clean the sample before quantification.

Hereunder, embodiments of the invention are presented, which have been included for the purpose of illustrating the invention, its preferred embodiments and comparative examples; but they must not be considered in any case to restrict the scope of the patent application, which is only limited by the content of the claims appended hereto.

EXAMPLES

Example 1: Selection of the Immobilizing Support for the β-Glucuronidase Enzyme from Different Origins Agarose was selected as test polymer for the immobilization support. An assay of enzyme immobilization was performed with β-glucuronidase from *Haliotis rufescens* (BG100®, KuraBiotec) and from *Brachyspira pilosicoli* (BGTurbo™, KuraBiotec), using agarose activated with the functional chemical groups N-hydroxysuccinimide (Ag-NHS), amino (Ag-$NH_2$) or aldehyde, specifically glyoxyl groups (Ag-Gx) as testing supports.

Immobilization on Ag-$NH_2$: 1 g of Ag-$NH_2$ was added to 10 mL of the enzyme solution (0.2 mg/mL) in 10 mM sodium phosphate at 4° C., and incubated for 30 min. Subsequently the immobilized enzyme was filtered and washed with abundant distilled water.

Immobilization on Ag-NHS: 1 g of Ag-NHS was added to 10 mL of the enzyme solution (0.2 mg/mL) in 50 mM sodium phosphate at 4° C., and incubated for 2 h. Subsequently the immobilized enzyme was filtered and washed with 50 mM phosphate buffer with 500 mM NaCl.

Immobilization on Ag-Gx: 1 g of Ag-Gx was added to 10 mL of an enzyme solution (0.2 mg/mL) in 100 mM sodium bicarbonate at 4° C., and incubated for 3 h. To generate covalent bonds between the enzyme and the support, 10 mg of $NaBH_4$ were added and incubated for 0.5 h. Subsequently the immobilized enzyme was filtered and washed with 50 mM phosphate buffer with 500 mM NaCl in order to remove the protein not covalently immobilized.

The following Tables 1 and 2 show the results of immobilizing the enzymes mentioned, evaluated based on different parameters. The enzyme activity was determined using phenolphthalein β-D-glucuronide (PPG) as substrate.

TABLE 1

Immobilization of β-glucuronidase from *Haliotis rufescens* (BG100 ®, KuraBiotec).

| Support | Method | Activity yield (%) | Protein yield (%) | Enzyme activity (U/g) | Protein loading (mg/g) |
|---|---|---|---|---|---|
| Ag—$NH_2$ | Adsorption | 26 | 37 | 819 ± 22 | 0.85 ± 0.03 |
| Ag—NHS | covalent bonding | 0 | 13 | 0 | 0.24 ± 0.02 |
| Ag—Gx | covalent bonding | 89 | 44 | 3,191 ± 806 | 0.83 ± 0.03 |

TABLE 2

Immobilization of β-glucuronidase from *Brachyspira pilosicoli* (BGTurbo ™, KuraBiotec).

| Support | Method | Activity yield (%) | Protein yield (%) | Enzyme activity (U/g) | Protein loading (mg/g) |
|---|---|---|---|---|---|
| Ag—$NH_2$ | Adsorption | 95 | 98 | 71,894 ± 11,513 | 0.67 ± 0.02 |
| Ag—NHS | covalent bonding | 19 | 45 | 23,193 ± 1,034 | 0.28 ± 0.01 |
| Ag—Gx | covalent bonding | 97 | 98 | 85,665 ± 694 | 0.80 ± 0.01 |

From the previous results it is shown that, although it was possible to immobilize both enzymes on agarose polymers with different modifications of chemical functional groups, the best result in terms of performance and enzyme activity is obtained when the β-glucuronidase enzymes are immobilized on agarose modified with glyoxyl groups (Ag-Gx), so this variant was chosen for the following experimental stages.

Example 2: Stabilization of β-Glucuronidase Enzymes from Different Sources

Figure 4A:
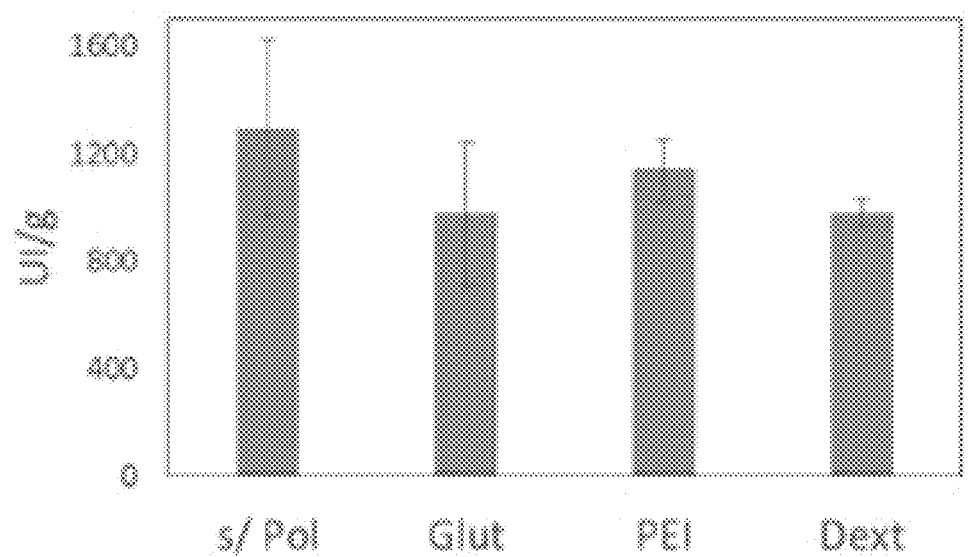
FIGS. 4A and 4B show the enzymatic activity of the BG100® and BGTurbo™ enzymes, respectively, stabilized with different agents.
Figure 4B:
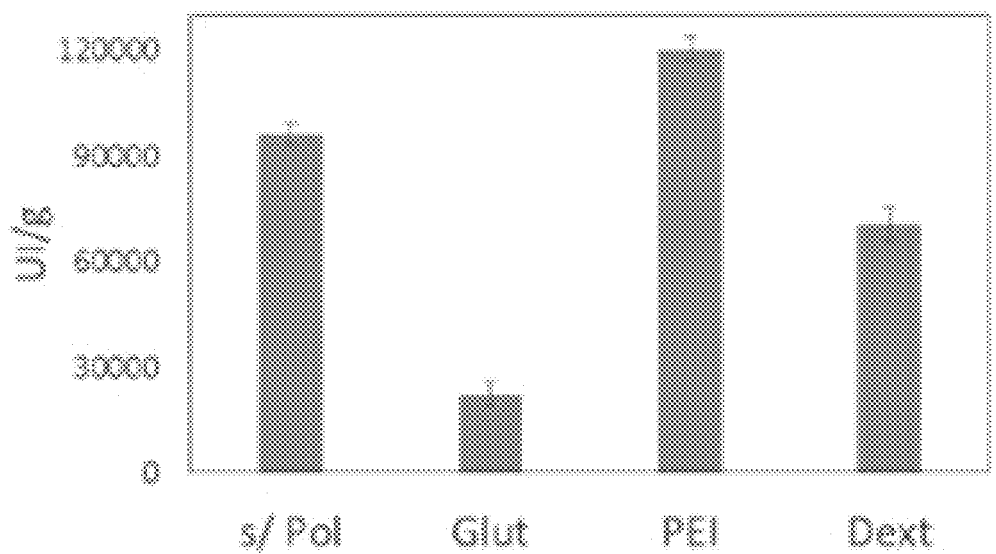

To stabilize the quaternary structure of the previously immobilized enzymes, different agents were tested for crosslinking the same in the resin. The BGTurbo™ and BG100® enzymes (KuraBiotec) immobilized on agarose modified with glyoxyl groups (Ag-Gx) were crosslinked with different stabilizing agents (glutaraldehyde (Glut), polyethyleneimine (PEI) and dextran-aldehyde (Dext)) and the enzyme activity was measured. The immobilized un-crosslinked enzymes (s/Pol, without polymers) were used as a control. As shown in FIGS. 4A and 4B, wherein the results obtained for BG100® and BGTurbo™ are shown respectively, enzymes immobilized and stabilized by crosslinking with polyethyleneimine (PEI) possess an enzymatic activity superior to other agents tested. It is important to highlight that by using the β-glucuronidase enzyme from *Brachyspira pilosicoli* (BGTurbo™) immobilized on agarose modified with glyoxyl groups and stabilized with polyethyleneimine, the enzymatic activity is higher than that obtained in the control condition, when the enzyme is not stabilized with polyethyleneimine (s/Pol) (FIG. 4B).

Example 3: Enzyme Immobilization and Stabilization with Polyethyleneimine of Different Sizes To select the size of polyethyleneimine polymer to be used, it was measured the enzymatic activity of β-glucuronidase from *Brachyspira pilosicoli* (BGTurbo™, KuraBiotec) and *Haliotis rufescens* (BG100®, KuraBiotec), previously immobilized on agarose modified with glyoxyl groups (Ag-Gx) and incorporating variants of different sizes of branched polyethyleneimine from 1.2 kDa to 60 kDa, corresponding to the number average molecular weight of said branched polymers. The enzyme activity measured using PPG as a substrate is shown in FIGS. 5A and 5B, wherein the activity obtained with BG100® and BGTurbo™ are shown respectively; while FIGS. 5C and 5D show a gel electrophoresis (SDS-PAGE) to determine stabilization of the quaternary structure of the immobilized and stabilized BG100® and BGTurbo™ enzymes, respectively. Gel electrophoresis of 12% polyacrylamide was performed under denaturing conditions (SDS-PAGE) (Laemmli, U. (1970). Relevant page on gel electrophoresis. Nature, 227, 681), for which 100 μL of rupture buffer were added to each sample and incubated at 100° C. for 5 min. The sample with the insoluble enzyme was centrifuged for 1 minute at 5,000 rpm, and the supernatants of the samples were injected into the polyacrylamide gel; and after the electrophoretic run the gel was stained with Coomassie blue.

FIG. 5A shows that the enzyme BG100® immobilized on Ag-Gx and stabilized with polyethyleneimine (PEI) of different sizes has similar activity, between 866 and 1,336 U/g; while the stability of the quaternary structure was achieved using PEI polymers between 10 kDa and 60 kDa (FIG. 5C), since when using 1.2 kDa PEI it is observed loss of enzyme monomers (75 kDa bands) as in the control condition where no PEI polymer (S/Pol) was used.

Similarly, in studies using BGTurbo™ (FIGS. 5B and 5D), when immobilized and stabilized with PEI polymers between 10 kDa and 60 kDa, the enzyme increased its activity even more than the immobilized but un-crosslinked variant (s/Pol) as shown in FIG. 5B. When analyzing the stabilization of the quaternary structure, it is observed that the three polymer sizes tested produce the stabilization of the multimeric structure of the enzyme, since loss of monomers of 75 kDa (FIG. 5D) was not observed. This is advantageous in the case of performing a subsequent quantization by chromatography, as the sample to be analyzed will not produce noise in the signal.

To summarize, the following Table 3 shows the results of the immobilization and stabilization of β-glucuronidase enzymes.

TABLE 3

Immobilization of β-glucuronidase enzymes on Ag—Gx and PEI (60 kDa).

| Insolubilized enzyme reagent | Specific activity (U/g) * | Protein immobilized on the support (mg/g) | Immobilization yield (measured in activity) (%) |
|---|---|---|---|
| BG100 ® | 1,124 ± 122 | 0.94 ± 0.03 | 90 |
| BGTurbo ™ | 134,941 ± 5.783 | 1.5 ± 0.03 | 96 |

* The specific activity was measured using PPG as substrate.

Example 4: Immobilization and Stabilization of β-Glucuronidase Enzymes

To obtain the agarose support modified with glyoxyl groups, the protocol of Guisán, J. (1988), *Aldehyde-agarose gels as supports for activated immobilization-stabilization of enzymes, Enzyme and Microbial Technology*, 10 (6), 375-382 was used with modifications. First, the agarose gel was activated with glycidol to produce ether linkages, then glyoxyl groups were generated with an oxidizing agent to obtain the modified agarose (Ag-Gx); subsequently, the enzyme with glucuronidase activity was incorporated and then a solution of polyethyleneimine was added to enhance the stabilization of the enzyme on the support. Another agent capable of generating glyoxyl groups is epichlorohydrin, which can replace the glycidol.

Further details of each of the steps required for immobilizing an enzyme with glucuronidase activity, as part of the present invention, are given below.

Activation of Agarose Gel (Ag)

This step allows the activation of the side chains of the agarose and then to anchor the enzyme in this matrix. An amount of 100 g of crosslinked agarose (Sepharose 6BCL™, Sigma Aldrich) was weighed and added to 50 mL of 1.7N NaOH solution. Then 1.5 g of $NaBH_4$ were added and the mixture was homogenized. A volume of 36 mL of glycidol (100%) was added and mixed for 15 hours. The mixture was filtered and washed with abundant water.

Preparation of Glyoxyl Groups (Gx).

A volume of 1.5 L of a sodium periodate ($NaIO_4$) 10 mM solution was added to 100 g of previously activated agarose and stirred for 2 hours. The mixture was filtered and washed with abundant water.

Preparation of Polyethyleneimine (PEI) Polymer.

A 25 mg/mL PEI solution was prepared, to which 0.5 g were taken from a solution of polyethyleneimine 50% (60 kDa) (Polyethyleneimine solution, Sigma Aldrich), number average molecular weight 60 kDa, and average molecular weight 750 kDa; and 9 mL of 100 mM bicarbonate buffer were added. The mixture was stirred to dissolve the PEI and diluted to 10 mL with bicarbonate buffer.

Immobilization and Stabilization of the Enzyme with Glucuronidase Activity.

An enzyme solution was prepared at 0.2 mg/mL to obtain a load of 2 mg of enzyme per gram of support. A volume of 11 mL was taken of the above enzymatic solution in 100 mM bicarbonate buffer. To a quantity of 1 g of agarose modified with glyoxyl groups from the previous step (Ag-Gx) 10 mL of the enzyme solution were added and incubated under stirring at 4° C. for 3 hours. The mixture of the support with the recovered enzyme (approximately 1 g) was filtered without washing and 5 mL of polyethyleneimine solution (25 mg/mL) in bicarbonate buffer 100 mM were added. Incubation was performed with stirring at 4° C. for 3 hours.

Then, 5 mg of NaBH$_4$ were added and allowed to react for 30 minutes. The mixture was filtered and washed with abundant water.

Example 5: Immobilization of β-Glucuronidase from *Brachyspira pilosicoli* Improved Enzyme Activity Compared to the Enzyme in Soluble Form Thermal Stability Assay.

It was performed a test of thermal stability of the β-glucuronidase enzyme from *Brachyspira pilosicoli* (BG-Turbo™, KuraBiotec) immobilized on the resin of agarose modified with glyoxyl groups and polyethyleneimine of the present invention, and compared with the same enzyme but in soluble form, i.e., not immobilized. For this assay, a suspension of the immobilized enzyme was prepared (or a solution of the soluble enzyme) in 100 mM citrate buffer; the samples were incubated at 60° C. and then samples were taken to measure activity at different times.

Figure 6A:
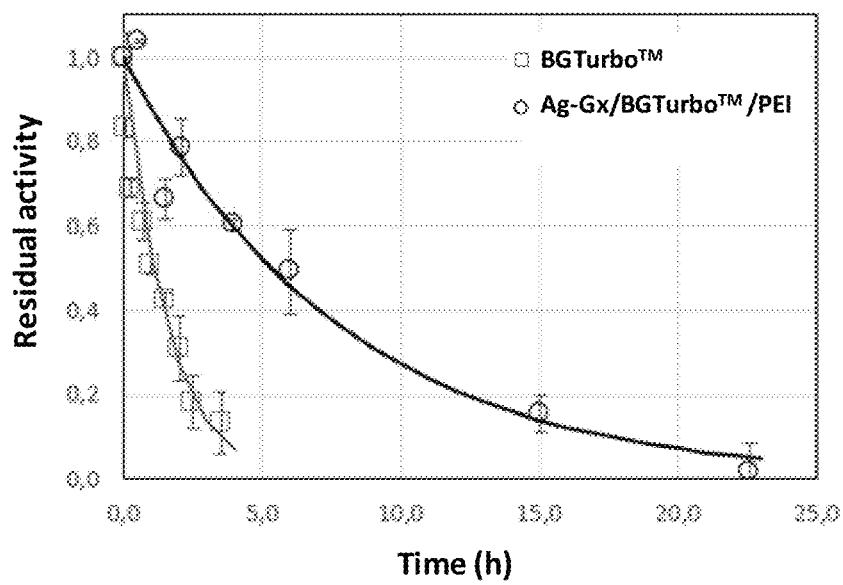
FIG. 6A shows a plot of the time-residual activity of a soluble β-glucuronidase enzyme in comparison to the immobilized form.

The obtained results showed that the immobilized β-glucuronidase enzyme maintained its activity for a period longer than 15 hours; while the soluble enzyme (not immobilized) lost its activity before 5 hours, as shown in FIG. 6A.

Figure 6B:
FIG. 6B shows the inactivation kinetics of the same enzyme in soluble and immobilized form.

Subsequently, the inactivation kinetics of the immobilized β-glucuronidase enzyme was compared to the soluble form and calculated with the data obtained in the thermal stability assay. Data were fitted to different models of inactivation; however, the best fit was the model of first-order inactivation. FIG. 6B shows the kinetic parameters of the transition from the folded enzyme (E) form to the denatured state (D). As shown in this figure, the immobilized enzyme has a dissociation constant ($k_1$) five times lower than the soluble enzyme, indicating that it inactivates much slower. Consequently, the half-life ($t_{1/2}$) defined as the time required for the activity to be reduced by half, of the immobilized enzyme also increased five times in comparison with the soluble variant.

Enzyme Activity in a Range of pH and Temperature.

Figure 7A:
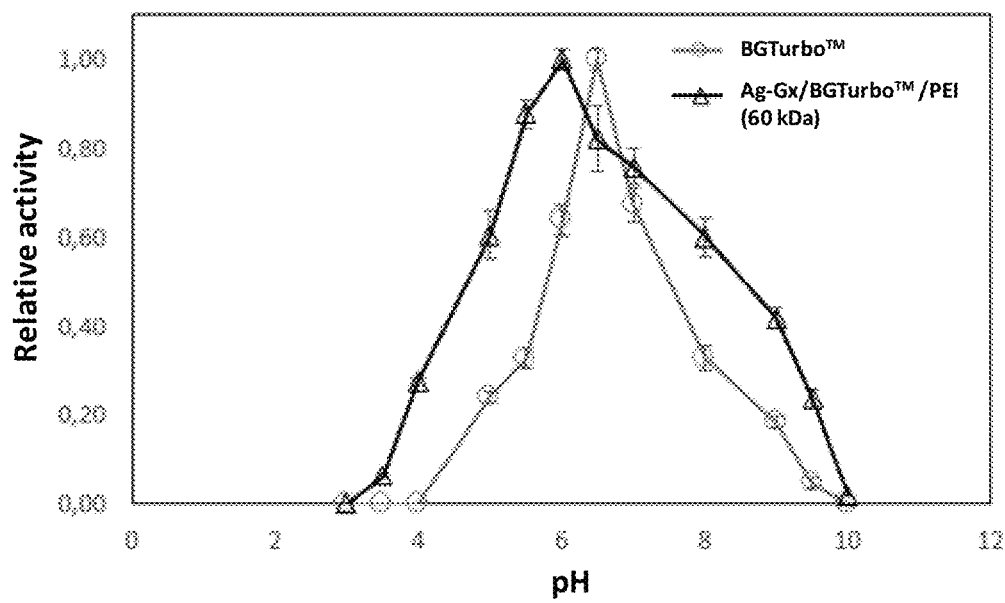
FIG. 7A shows a graph of the relative activity of the soluble or immobilized enzyme β-glucuronidase from *Brachyspira pilosicoli* as a function of pH.

It was performed a comparison between the activity of the β-glucuronidase enzyme from *Brachyspira pilosicoli* (BG-Turbo™, KuraBiotec) immobilized in comparison with the soluble variant without being immobilized. The compound p-nitrophenyl-β-glucuronide (pNPG) was used as substrate for the hydrolysis reaction and the increase in absorbance at 348 nm was measured, resulting from the formation of p-nitrophenol as the product, in 50 mM sodium phosphate buffer with 1% w/v of bovine serum albumin (BSA) at 37° C. during a 30 minutes reaction. To start the reaction, 0.01 mL of the soluble enzyme or 0.1 mL of the suspension with the immobilized enzyme were added to 2 mL of 0.5 mM substrate solution. Enzymatic activity was measured, where an international activity unit (IU) on pNPG is defined as the amount of enzyme required to hydrolyze 1 μmol of substrate per minute under the previously mentioned conditions. Relative enzymatic activity was quantified versus pH, for which 100% was considered as the activity obtained under the conditions previously mentioned. As shown in FIG. 7A, the β-glucuronidase enzyme in both conditions showed activity in the pH range from 3 to 10, however, the immobilized enzyme showed a much higher enzyme activity throughout the range, when compared to the soluble form. This allows to use a greater variety of buffer solutions with higher pH range, or solutions having a lower ion concentration, facilitating compatibility with different systems of extraction and quantification.

Figure 7B:
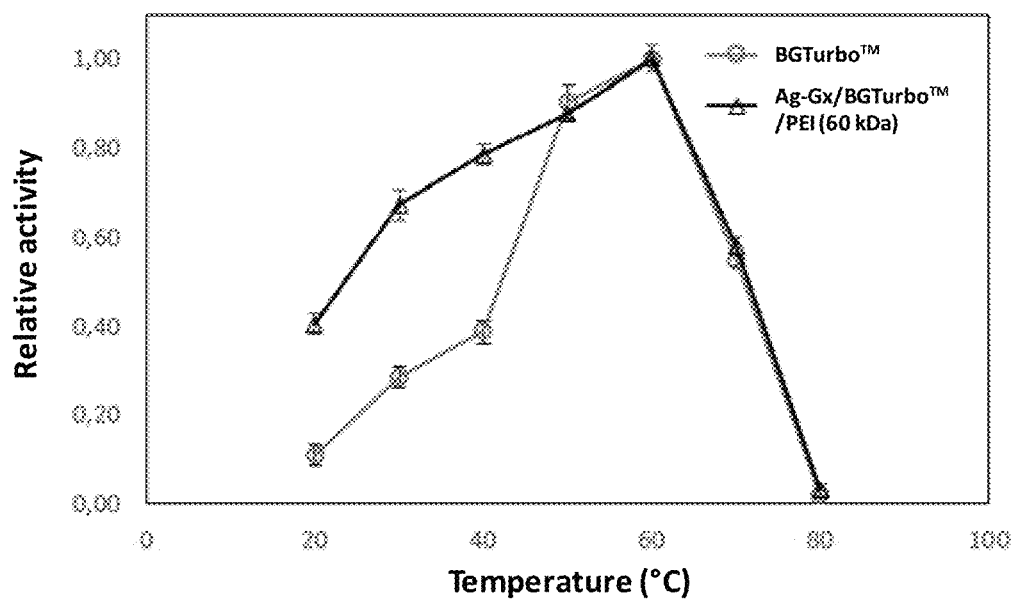
FIG. 7B shows a graph of the relative activity of the soluble or immobilized enzyme β-glucuronidase *Brachyspira pilosicoli* as a function of temperature.

Subsequently, a test similar to the previous was performed; but varying the temperature range. As shown in FIG. 7B, the activity of the immobilized β-glucuronidase enzyme was 3 to 4 times higher than the soluble enzyme in the temperature range 20-50° C. This represents an important advantage, since by using the immobilized variant, the amount of enzyme required to hydrolyze the same amount of substrate is reduced; and further it allows to carry out the hydrolysis process without the need to incubate at a higher temperature.

Example 6: Proof of Concept of the Insoluble Enzymatic Reagent in Different Columns Application of the Resin with the Immobilized β-Glucuronidase Enzyme in a Column of Hydrolysis.

Figure 8:
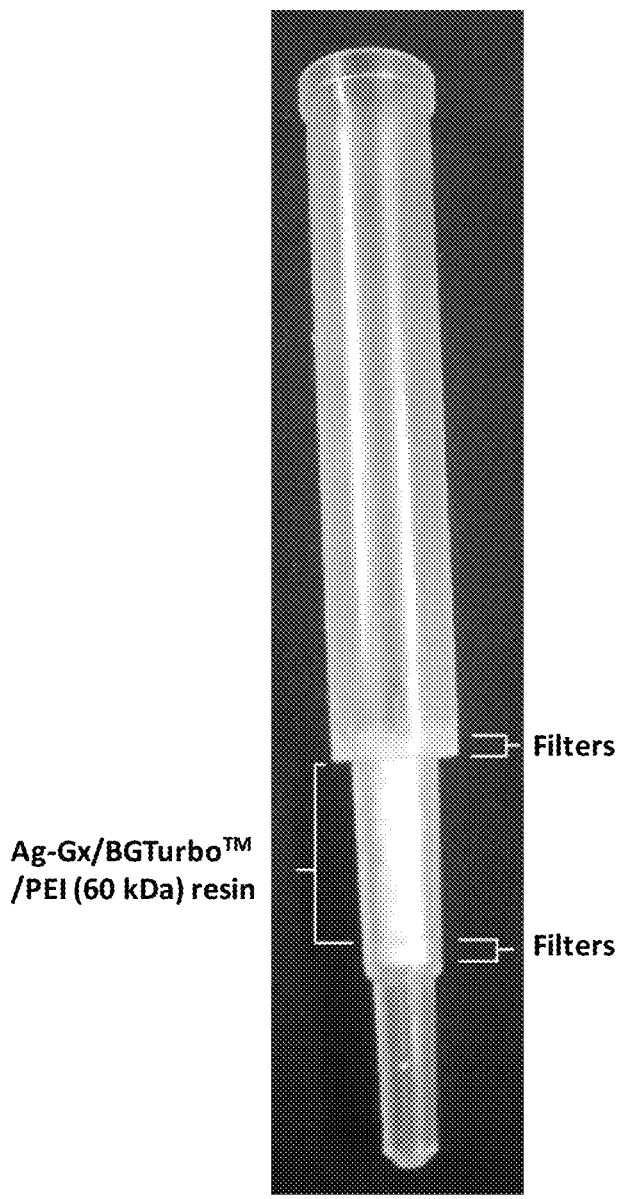
FIG. 8 shows a β-glucuronidase enzyme immobilized as an insoluble enzymatic reagent and used as a hydrolysis column.

It was used an empty polypropylene column (Narrow Bore Extraction column, SPEware™) with a narrow inner pore diameter of 1 mm, to which 34 mg of agarose-glyoxyl-8-glucuronidase-PEI (60 kDa) resin was added, containing the immobilized BGTurbo™ (KuraBiotec) β-glucuronidase enzyme in a concentration of 2 mg of enzyme/gram of resin, as insoluble enzymatic reagent. Below the resin, a 10 μm filter was incorporated. The column fully assembled is shown in FIG. 8.

Subsequently, a solution consisting of enzyme substrate in 0.1 M phosphate buffer (350 μL), 0.64 mg/mL phenolphthalein β-D-glucuronide (PPG) (350 μL) and distilled water (50 μL) was prepared to obtain a 750 μL final volume. This solution was passed by continuous flow through the column including the resin with the immobilized enzyme (FIG. 7A). The hydrolysis products were collected in a test tube with 2.5 mL of 0.1 M glycine to stop the reaction, and absorbance at 540 nm was measured. The obtained results showed that the solution of enzyme substrate completely passed through the column in approximately 150 seconds at a flow rate of 0.3 mL/min to give 46.7% of released deconjugated phenolphthalein.

Application of the Resin with Immobilized the β-Glucuronidase Enzyme in a Column of Solid Phase Extraction DPX.

Figure 2:
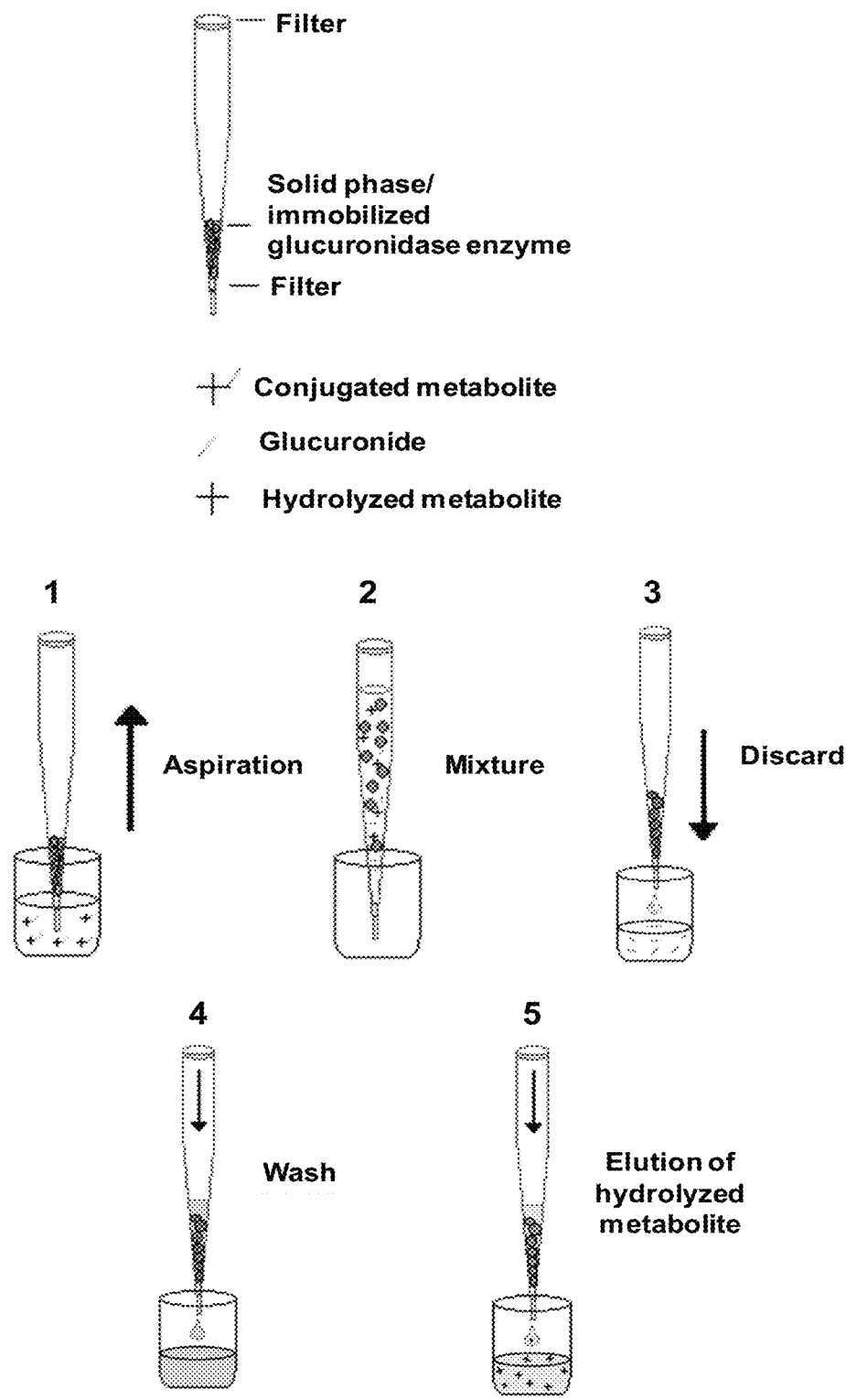
FIG. 2 depicts a solid phase extraction column (DPX) to which a glucuronidase enzyme immobilized on a resin as an insoluble enzymatic reagent has been incorporated, for the hydrolysis of compounds conjugated with glucuronides.
Figure 9:
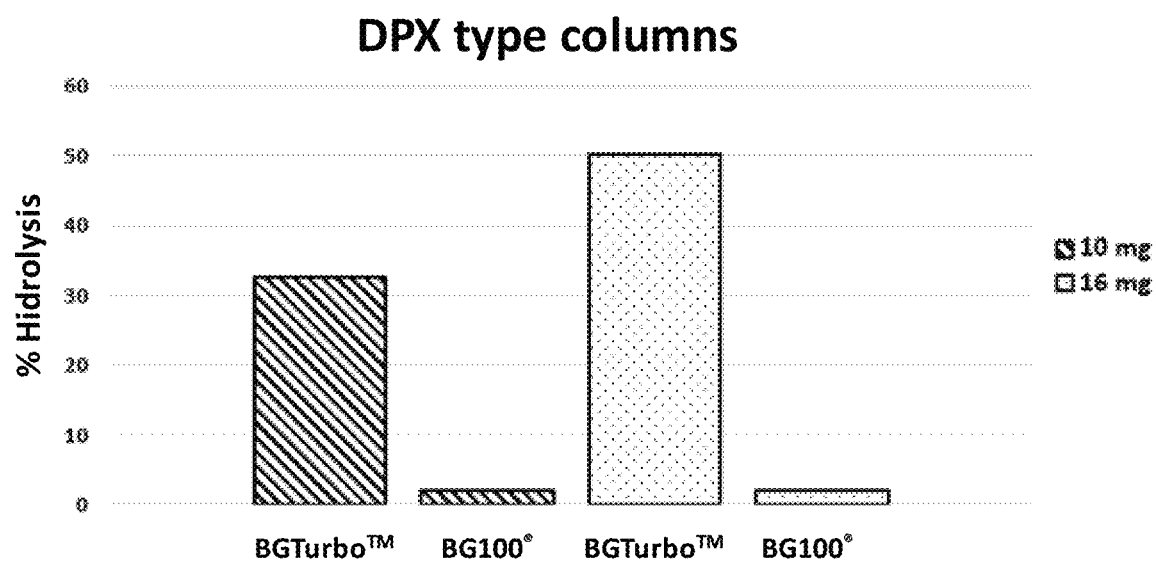
FIG. 9 shows the effect of urine on the enzymatic activity of immobilized β-glucuronidase enzymes.

The activity of two β-glucuronidase enzymes from the bacteria *Brachyspira pilosicoli* (BGTurbo™, KuraBiotec) and abalone *Haliotis rufescens* (BG100®, KuraBiotec) immobilized on agarose-glyoxyl resins and polyethyleneimine (PEI) (60 kDa) was tested, using phenolphthalein β-D-glucuronide (PPG) as substrate. Subsequently, each enzyme immobilized on the same type of resin was implemented in a dispersive solid phase extraction column system with DPX type disposable pipette tips (Disposable Pipette Extraction) (FIG. 2). A 750 μL reaction volume containing 350 μL of sodium phosphate (0.1 M), 350 μL of PPG (0.64 mg/mL) and 50 μL of distilled water was used. It was tested 10 and 16 mg of each resin containing immobilized β-glucuronidase. The hydrolysis reaction was carried out at 25° C. for two minutes and stopped with glycine (0.2 M). A negative control was used without enzyme, using this value as 0% hydrolysis. The results are shown in FIG. 9 and Table 4.

TABLE 4

Hydrolysis obtained by insoluble enzymatic reagents implemented in DPX type columns.

| Immobilized β-glucuronidase enzyme | Amount of resin | Percent of hydrolysis |
| --- | --- | --- |
| BGTurbo ™ | 10 mg | 32.7% |
| BG100 ® | 10 mg | 3.95% |

TABLE 4-continued

Hydrolysis obtained by insoluble enzymatic reagents implemented in DPX type columns.

| Immobilized β-glucuronidase enzyme | Amount of resin | Percent of hydrolysis |
|---|---|---|
| BGTurbo ™ | 16 mg | 51.39% |
| BG100 ® | 16 mg | 2.89% |

From the results of Table 4 and FIG. 9, it is observed that using 10 mg of the resin with the enzyme incorporated and immobilized (agarose-glyoxyl/BGTurbo™/PEI (60 kDa)), an activity of 32.7% hydrolysis of the substrate is obtained, while maximum activity was observed when 16 mg of said resin are used, achieving approximately 50% hydrolysis. By contrast, the hydrolytic activity of the β-glucuronidase enzyme from abalone (BG100®) immobilized on agarose-glyoxyl/BG100®/PEI (60 kDa) resin was very low, not exceeding 5% hydrolysis. These results indicate that the DPX type system can be used as a means for applying β-glucuronidase enzymes immobilized on resins for the hydrolysis of compounds conjugated with glucuronides.

Example 7: Tests for Immobilization and Stabilization of β-Glucuronidase Using Different Protein Loads It was prepared three concentrations variants of the enzyme immobilized on agarose modified with glyoxyl groups and polyethyleneimine resin, as shown in Table 5.

TABLE 5

Results of immobilization and stabilization of BGTurbo ™ at different protein loads.

| Immobilized enzyme (mg/g) | Enzyme activity (U/g)* | Activity yield (%) |
|---|---|---|
| 0.17 | 1,227 ± 241 | 93 |
| 1.48 | 162,538 ± 2,091 | 95 |
| 6.73 | 364,731 ± 1,508 | 43 |

*The specific activity was measured using PPG as substrate.

Similar results are observed with respect to performance (activity yield) of the amount of enzyme and the activity for the lower two loads (0.2 and 1.5 mg/g); and although there was a decrease when using the highest load, no enzyme activity was observed in the supernatant of the resin containing the immobilized enzyme.

Example 8: Assay of β-Glucuronidase Activity in the Presence of Urine

Figure 10:
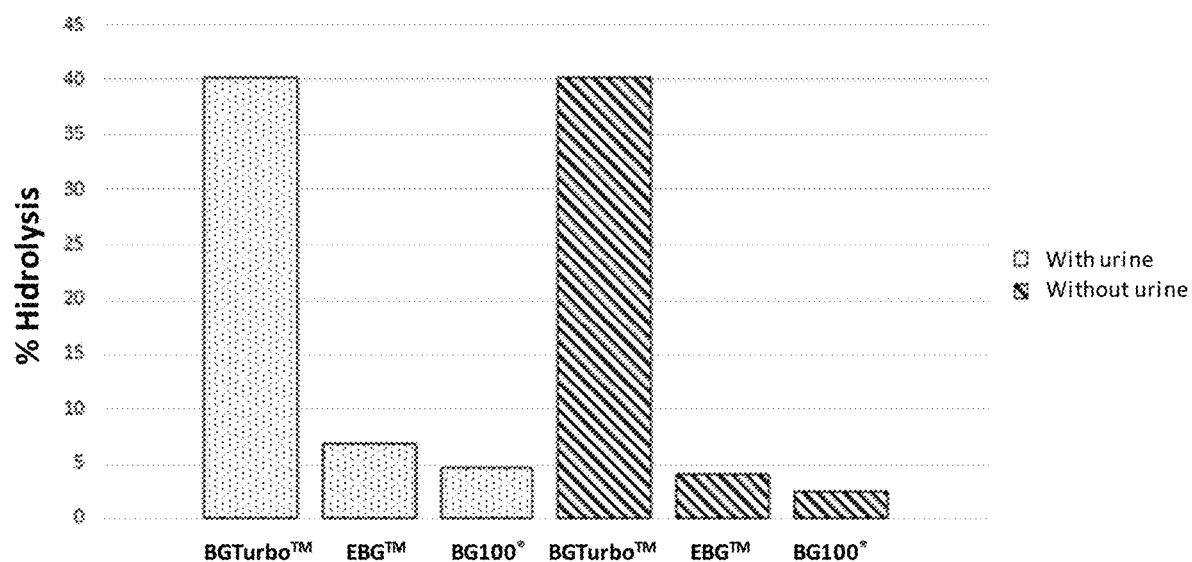
FIG. 10 shows a graph of the percent of hydrolysis in DPX-type columns, using the resin including β-glucuronidase enzymes in agarose-glyoxyl and polyethyleneimine (60 kDa).

Urine was used as the biological sample and the effect of said matrix was assessed on enzyme activity at 25° C. of β-glucuronidase enzymes from different origins (BG-Turbo™, *Brachyspira pilosicoli*; EBG™, *Escherichia coli*; BG100®, *Haliotis rufescens*, all obtained from KuraBiotec), immobilized on the resin of agarose activated with glyoxyl groups and crosslinked with PEI (60 kDa); and PPG used as substrate (1.28 mg/mL). As seen in FIG. 10, the urine does not modify the activity of the immobilized enzyme BGTurbo™, while the activity of enzymes of *E. coli* and *H. rufescens* decreases in the presence of urine.

The invention claimed is:

1. An insoluble enzymatic reagent for detecting products derived from glucuronide metabolites in a sample, comprising a β-glucuronidase enzyme originated from a bacterium of the genus *Brachyspira* sp., the enzyme being immobilized on a resin of a polysaccharide activated with an aldehyde functional group, wherein said polysaccharide is agarose and said aldehyde functional group is a glyoxyl group.

2. The reagent of claim 1, wherein said immobilized enzyme is cross-linked with polyethyleneimine.

3. The reagent of claim 1, wherein said immobilized enzyme is in a concentration ranging from 0.1 to 10 mg per gram of resin.

4. The reagent of claim 1, wherein the agarose has a particle size between 40 and 250 μm.

5. The reagent of claim 1, wherein the glyoxyl groups are in a concentration ranging from 10 to 100 μmol/mL of agarose.

6. The reagent of claim 2, wherein said polyethyleneimine is branched.

7. The reagent of claim 6, wherein said branched polyethyleneimine has a number average molecular weight ranging from 1 to 100 kDa; and a weight average molecular weight ranging from 1 to 1,000 kDa.

8. The reagent of claim 2, wherein said agarose and said polyethyleneimine are in a weight/weight (w/w) ratio ranging from 20:1 to 4:1.

9. The reagent of claim 1, wherein the β-glucuronidase enzyme is originated from the bacterium *Brachyspira pilosicoli*.

10. A method for preparing an insoluble enzymatic reagent for detecting products derived from glucuronide metabolites in a sample, comprising:
(i) providing a β glucuronidase enzyme originated from a bacterium of the genus *Brachyspira* sp.;
(ii) providing a resin of a polysaccharide activated with an aldehyde functional group, wherein said polysaccharide is agarose and said aldehyde functional group is a glyoxyl group; and
(iii) immobilizing the enzyme from step (i) by mixing it with the resin of step (ii).

11. The method of claim 10, further comprising:
(iv) adding to the mixture of step (iii) a solution of polyethyleneimine as a stabilizing agent, and
(v) adding a reducing chemical agent.

12. The method of claim 10, wherein the enzyme is in a concentration ranging from 0.01 to 10 mg/mL in a solution at alkaline pH ranging from 7 to 11.

13. The method of claim 10, wherein the agarose has a particle size between 40 and 250 μm.

14. The method of claim 10, wherein the agarose activated with the glyoxyl group and the enzyme are in a weight/weight (w/w) ratio ranging from 10,000:1 to 20:1.

15. The method of claim 11, wherein the polyethyleneimine solution has a concentration ranging from 1 to 100 mg/mL at alkaline pH between 7 and 11.

16. The method of claim 11, wherein the reducing chemical agent is a metal borohydride.

* * * * *